United States Patent [19]

McKendry et al.

[11] 4,419,514
[45] Dec. 6, 1983

[54] METHOD FOR CONVERTING CARBOXYLIC ACID GROUPS TO TRICHLOROMETHYL GROUPS

[75] Inventors: Lennon H. McKendry, Midland, Mich.; Michael J. Ricks, Martinez; Richard B. Rogers, Concord, both of Calif.

[73] Assignee: The Dow Chemical Company, Midland, Mich.

[21] Appl. No.: 264,491

[22] Filed: May 18, 1981

Related U.S. Application Data

[63] Continuation-in-part of Ser. No. 180,064, Aug. 21, 1980, abandoned.

[51] Int. Cl.$^3$ .................. C07D 239/02; C07D 211/72; C07D 211/84; C07D 213/26
[52] U.S. Cl. .................................. 544/334; 546/346; 546/345; 546/303; 546/312; 570/194; 570/195; 260/465 G; 568/936; 568/588
[58] Field of Search .............. 546/346, 345, 304, 297, 546/315, 286, 303, 312; 570/194, 195; 544/334; 260/465 G; 568/936, 588

[56] References Cited

U.S. PATENT DOCUMENTS

| | | | |
|---|---|---|---|
| 2,679,453 | 5/1954 | Brett et al. | 570/194 |
| 2,945,894 | 7/1960 | Earhart et al. | 570/195 |
| 3,173,919 | 3/1965 | Johnston et al. | 570/194 |
| 3,244,722 | 4/1966 | Johnston et al. | 570/194 |
| 3,251,849 | 5/1966 | Towita | 570/194 |
| 3,284,188 | 11/1966 | Awagasa et al. | 570/194 |
| 3,687,827 | 8/1972 | Seiber | 570/194 |
| 3,820,973 | 6/1974 | Noveroske | 570/194 |
| 3,937,831 | 2/1976 | Griffith et al. | 570/194 |

OTHER PUBLICATIONS

Chem. Abs., vol. 65, 1966, 65:11262f.
Chem. Abs., vol. 54, 1960, 54:16009i.
Chem. Abs., vol. 55, 1961, 55:14334d.
Chem. Abs., vol. 63, 1965, 63:14806g.

*Primary Examiner*—Richard Raymond
*Assistant Examiner*—Robert C. Whittenbaugh
*Attorney, Agent, or Firm*—S. Preston Jones; Ronald G. Brookens

[57] ABSTRACT

Method for converting carboxylic acid groups to trichloromethyl groups which comprises contacting a compound containing a carboxylic acid group with a phenylphosphonic dichloride and phosphorus pentachloride and recovering the thus produced product.

13 Claims, No Drawings

METHOD FOR CONVERTING CARBOXYLIC ACID GROUPS TO TRICHLOROMETHYL GROUPS

REFERENCE TO RELATED APPLICATION

This application is a continuation-in-part of application Ser. No. 180,064, filed Aug. 21, 1980, now abandoned.

BACKGROUND OF THE INVENTION

It is known to convert a ring attached carboxylic acid group to a trichloromethyl group when said acid group is on the ring of a nitrogen heteroaromatic compound and in a position adjacent to a ring nitrogen atom.

One reason for making such conversions is to allow for the preparation of compounds which cannot be prepared by the conventional practice of direct chlorination of methyl groups. For example, compounds containing alkoxy, alkyl or alkoxy or alkyl substituted aryl groups, in addition to the methyl group to be converted, cannot normally be prepared by direct chlorination without chlorination of the above groups.

Most known processes involve treatment of the carboxylic acid compound with phosphorus pentachloride usually in the presence of excess thionyl chloride. Such processes are taught by Takahashi et al. "Kinetic study on the conversion of pyridine and Quinolinecarboxylic acids to the corresponding Trichloromethyl Compound," J. Het. Chem. 15 893 (1978); Chemical Abstracts 74, 125566y; Chemical Abstracts 79 31986m and Chemical Abstracts 81 105395h. Related processes for other types of chlorinations are taught in Chemical Abstracts 63 9901d and U.S. Pat. No. 2,907,798.

Since the known procedures are only useful in the conversion of carboxylic acid groups to trichloromethyl groups when the acid group is adjacent to the nitrogen atom in a nitrogen heteroaromatic cyclic, it would be desirable to find less selective procedures and procedures which can be employed with other than nitrogen heteroaromatics.

SUMMARY OF THE INVENTION

The present invention is directed to a method for the conversion of carboxylic acid groups to trichloromethyl groups which comprises contacting an aryl or heteroaryl compound containing a carboxylic acid group with a phenylphosphonic dichloride and phosphorus pentachloride.

More specifically, the present invention is directed to a method for the conversion of any carboxylic acid groups on an aryl or heteroaryl ring to trichloromethyl groups by reaction thereof with a phenyl phosphonic dichloride and phosphorus pentachloride. This reaction can be characterized as follows:

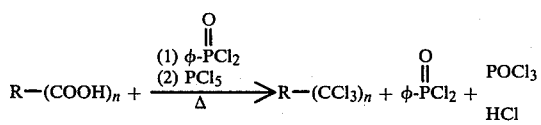

wherein R represents aryl or N-heteroaryl and n is 1 or 2. (No attempt has been made to present a balanced equation.)

The aryl or N-heteroaryl carboxylic acid compounds useful in the present process can be any aryl or N-heteroaryl compound containing one or two carboxylic acid groups in non-sterically hindered ring positions and which compound is substantially chemically and physically stable under the acidic conditions of the reaction with the exception of the conversion of the carboxylic acid groups to the corresponding trichloromethyl groups. When there are two acid groups present they should be in nonadjacent ring positions to avoid steric hindrance problems.

The compounds can in addition be ring substituted with additional sterically compatible groups which are non-reactive under the conditions of the reaction such as chloro, fluoro, nitro, cyano, alkyl, alkoxy, alkylthio, aryl, alkyl substituted aryl, alkoxy substituted aryl, aryloxy, trichloromethyl or trifluoromethyl. To further insure that problems of steric hindrance be avoided, it is important that no groups having an atom radius larger than the atom radius of a chlorine atom be adjacent to a carboxylic acid group. Further, if an alkyl, alkylthio or alkoxy group is substituted on an aryl ring, it is necessary that a strong electron withdrawing group such as nitro or cyano be also on the ring. This latter requirement is not necessary for N-heteroaromatic compounds.

In the present specification and claims, the term "sterically compatible" is employed to designate substituent groups which are not affected by steric hindrance as defined in "The Condensed Chemical Dictionary," 7th edition, Reinhold Publishing Co. N.Y., page 893 (1966) which definition is as follows:

"steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in "Organic Chemistry" D. J. Cram and G. Hammond, 2nd edition, McGraw-Hill Book Company, N.Y., page 215 (1964).

In carrying out the present process, the order of the addition of the reactants is not critical although in some situations, one mixing procedure may be more desirable than another. For example, if the reaction is to be run on a large scale, it is helpful to allow the carboxylic acid compound and the phenyl phosphonic dichloride compound to react for a period of time (until HCl evolution ceases) before adding the phosphorus pentachloride. This allows for more control of any initial foaming which might occur and more control of the exothermic nature of the reaction. In other situations, all the reactants can be mixed together.

After the reactants are mixed, the mixture is heated at reflux, ~100°–~250° C. The process is usually carried out at atmospheric pressure; however, the reaction goes well at pressures of from about 0.1 to about 10 atmospheres.

The reaction is usually completed in from about 4 hours to about 7 days, dependent upon the temperature, reactants and amounts of reactant. Upon the completion of the reaction, the reaction mixture is cooled and the phosphorus oxychloride byproduct is removed by distillation under reduced pressure. The desired product can be separated and recovered by conventional techniques such as by fractional distillation under reduced pressure or by solvent extraction after the reaction mixture was made basic with dilute base. The product can be purified if desired by conventional techniques such as by water washing, drying and recrystallization from a solvent such as benzene, hexane, methanol, chloroform, ether, cyclohexane or acetonitrile.

The phenylphosphonic dichlorides are usually present in an amount of from about 0.1 to about 20 molar equivalents of the phenylphosphonic dichloride per carboxylic acid group on the carboxylic acid compound. Preferably, from about 1 to about 10 molar equivalents of the phenylphosphonic dichloride per carboxylic acid group is employed.

Representative of those phenylphosphonic dichlorides which can be employed in the practice of the present invention include those corresponding to the formula

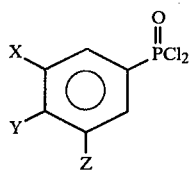

wherein X, Y and Z independently represents hydrogen, fluoro, chloro, cyano, trifluoromethyl, nitro and alkyl sulfonyl of 1 to 4 carbon atoms.

The phosphorus pentachloride is usually present in an amount of from about 2 to about 10 molar equivalents of the phosphorus pentachloride per carboxylic acid group on the carboxylic acid compound. Preferably, from about 2 to 5 molar equivalents of the phosphorus pentachloride per carboxylic acid group is employed. If the carboxylic acid compound is ring substituted with a reactive group such as bromo, iodo or hydroxy group, an additional molar equivalent of the phosphorus pentachloride is necessary for each such group. These reactive groups are normally replaced with chlorine.

DESCRIPTION OF SOME PREFERRED EMBODIMENTS

The following examples illustrate the present invention and the manner by which it can be practiced but, as such, should not be construed as limitations upon the overall scope of the same.

EXAMPLE I

Preparation of 4-chloro-2,6-bis(trichloromethylpyridine).

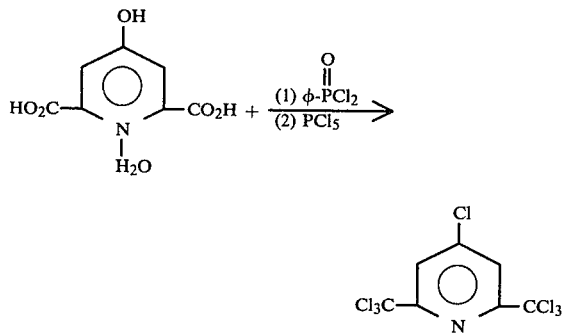

To a 5-liter flask equipped with a mechanical stirrer, thermometer and condenser was added 1950 grams (g) (10 moles (m)) of phenylphosphonic dichloride. Thereafter 302 g (1.5 m) of 2,6-dicarboxy-4-hydroxypyridine monohydrate (chelidamic acid monohydrate) was rapidly added. The mixture was slowly and carefully heated to 150° C. over a two hour period. Thereafter, the mixture was cooled to 50°–60° C. and 1029 g (5.25 m) of phosphorus pentachloride was rapidly added. The mixture was heated until the internal temperature was 75°–80° C. and the heat source removed. The temperature exothermically rose to ~125° C. and after a short period, the temperature started to cool. When the reaction mixture reached a temperature of 90° C., a second portion of phosphorus pentachloride (1029 g (5.25 m) was added and the mixture heated at reflux (~140°–145° C.) for 12 hours. The condenser was replaced with a distilling head and the reaction mixture was distilled and the by-product phosphorus oxychloride was distilled off until a pot temperature of 215° C. was reached. At this point, the distilling head was replaced with a short fractionating column and phenyl phosphonic dichloride was rapidly distilled off at 75°–85° C. and 0.05 millimeters of mercury (mm Hg). The crude 4-chloro-2,6-bis(trichloromethyl)pyridine which remained solidified upon standing, and recrystallization of this material from methanol gave 314 g (60 percent of theoretical). The product melted at 101°–102° C. and its structure was confirmed by its Nuclear Magnetic Resonance spectra (NMR).

In other runs, this compound was prepared in yields as high as 85 percent of theoretical.

EXAMPLE II

Preparation of 1-nitro-4-(trichloromethyl)benzene

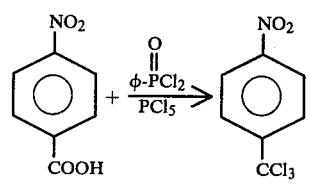

A mixture was prepared by adding with stirring and in the following order, 16.7 g (0.1 m) of 4-nitrobenzoic acid, 15.7 g (0.11 m) of phenylphosphonic dichloride and 52 g (0.25 m) of phosphorus pentachloride. The mixture was heated and stirred and within 1 to 2 minutes, vigorous HCl evolution began and the mixture became a clear yellow liquid. The reaction mixture was heated at reflux for ~15 hours, cooled to 25° C. and the phosphorus oxychloride byproduct was removed by evaporation under reduced pressure. The oil which remained as a residue was cautiously poured into a 10% solution of sodium carbonate in cold water and stirred vigorously until foaming ceased while maintaining the temperature below 30° C. The resultant solid crude 1-nitro-4-(trichloromethyl)benzene was recovered by filtraton, washed with water, air dried and recrystallized from hexane to give 19.6 grams (81 percent of theoretical) of product. The product melted at 44°–47° C. and its structure was confirmed by NMR.

In other runs, this compound was prepared in yields as high as 94 percent of theoretical.

EXAMPLE III

Preparation of 2,3-dichloro-5-(trichloromethyl)pyridine

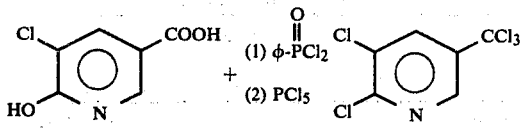

To a 5-liter flask equipped with an air stirrer, thermometer, and condenser was added 1000 grams (5.13 m) of phenylphosphonic dichloride. Thereafter, 383 g (2.707 m) of 5-chloro-6-hydroxynicotinic acid (prepared by bubbling chlorine into a stirred aqueous suspension of 6-hydroxynicotinic acid) was added. The mixture was slowly heated and stirred over a 20 minute period, with the temperature rising to 73° C. The mixture was in the form of a thick paste.

To this mixture was slowly added 1755 g (8.4 m) of phosphorus pentachloride over a 45 minute period. The hydrogen chloride by-product which formed was continuously removed and the heat was adjusted to maintain the temperature in the range of 83°–108° C. After the phosphorus pentachloride addition was complete, the mixture was heated to reflux and some of the phosphorus oxychloride by-product which formed was allowed to distill off. After a period of about 70 minutes, the temperature had exothermically risen to 169° C. and the temperature was held in the range of 162°–180° C. for 5¾ hours. During the above time additional phosphorus oxychloride was intermittently removed. The mixture was allowed to stand overnight and then poured over cracked ice, neutralized with 50 percent sodium hydroxide solution and the product extracted with hexane. The solvent was removed by evaporation under reduced pressure leaving 567 g of crude 2,3-dichloro-5-(trichloromethyl)pyridine.

The crude product was placed on a 15 tray vacuum jacketed Oldershaw distillation column and the light ends removed. The pot material was transferred to a Vigreux Claisen still and flash distilled to yield of 518 g (88.5 percent of theoretical) of a colorless oil which analysed as 99 percent pure 2,3-dichloro-5-(trichloromethyl)pyridine. Upon analysis the product was found to have carbon, hydrogen, chlorine and nitrogen contents of 26.99, 0.76, 66.49 and 5.23 percent respectively, as compared with the theoretical contents of 27.15, 0.76, 66.81 and 5.28 percent respectively, as calculated for the above named compound.

In Examples I, II and III, no attempt has been made to present balanced and complete reaction schemes.

By following the procedures as outlined in Examples I, II and III, the following compounds set forth below in Table I are prepared.

TABLE I

| Compound | Yield in Percent | Physical Property |
|---|---|---|
| C₆H₅–CCl₃ | 81 | $n\frac{20}{d} = 1.5566$ |
| 3-NO₂-C₆H₄–CCl₃ | 74 | $n\frac{25}{d} = 1.5800$ |
| 4-NC-C₆H₄–CCl₃ | 72 | $n\frac{25}{d} = 1.5755$ |
| 3-Cl₃C-C₆H₄–CCl₃ | 94 | M.P. = 104°–107° C. |
| 3-NO₂-4-CH₃-C₆H₃–CCl₃ | 67 | $n\frac{25}{d} = 1.5758$ |
| 3-O₂N-4-CH₃-C₆H₃–CCl₃ | 57 | $n\frac{25}{d} = 1.5784$ |
| 3-NO₂-4-C₄H₉-C₆H₃–CCl₃ | | |
| 3-O₂N-4-OC₄H₉-C₆H₃–CCl₃ | | |
| 2-F-C₆H₄–CCl₃ | 75 | $n\frac{25}{d} = 1.5411$ |
| 3-O₂N-4-OCH₃-C₆H₃–CCl₃ | 42 | $n\frac{25}{d} = 1.5836$ |
| 4-F₃C-C₆H₄–CCl₃ | | B.P. = 218° C. @ 760 mm |
| naphthyl–CCl₃ | | |
| 2-pyridyl–CCl₃ | | B.P. = 84°–86° C. @ 1 mm |
| 4-pyridyl–CCl₃ | | wt. crystals |

TABLE I-continued
| Compound | Yield in Percent | Physical Property |
|---|---|---|
| 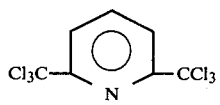 | | M.P. = 82°–84° C. |
| 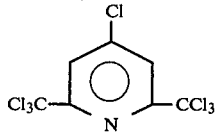 | 85 | M.P. = 101°–102° C. |
| 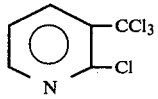 | | |
| 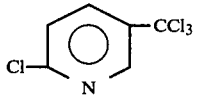 | 82 | M.P. = 52°–54° C. |
| 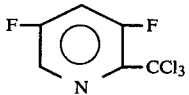 | | |
| 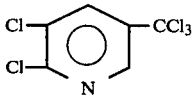 | 81 | $n\frac{25}{d} = 1.5863$ |
| 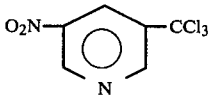 | | |
| 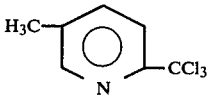 | | |
| 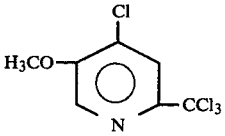 | | |
| 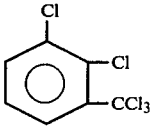 | | $n\frac{25}{d} = 1.5965$ |
| 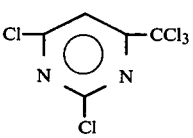 | | Yellowish Solid |
| 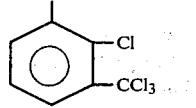 | | |
TABLE I-continued
| Compound | Yield in Percent | Physical Property |
|---|---|---|
| 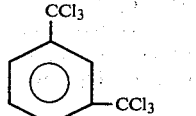 | | M.P. = 135°–137° C. |
| 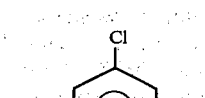 | | B.P. = 153°–155°/3 mm |
| 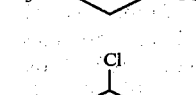 | | M.P. = 75°–77° C. |
| 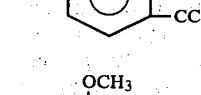 | | M.P. = 77°–79.5° C. |
| 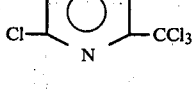 | | M.P. = 68°–69° C. |
| 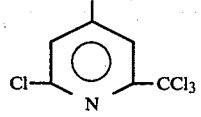 | | oil |
| 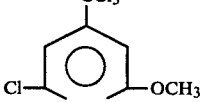 | | oil |
| 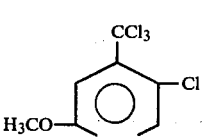 | | oil |
| 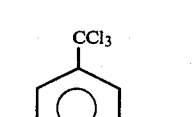 | | B.P. = 101°–103° C./24 mm |
| 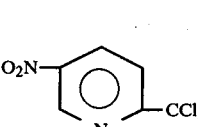 | | M.P. = 88°–91° C. |
| 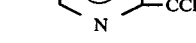 | | |

TABLE I-continued

| Compound | Yield in Percent | Physical Property |
|---|---|---|
| Cl-[pyridine]-Cl, CCl₃ | | M.P. = 33°–35° C. |
| Cl-[pyridine]-Cl, CCl₃ | | M.P. = 47.5°–48° C. |
| [pyridine with CCl₃, Cl, Cl] | | M.P. = 56°–58° C. |
| Cl, Cl-[pyridine]-CCl₃ | | M.P. = ~38° C. |
| Cl, Cl-[pyridine]-CCl₃ (with Cl) | | B.P. = 100–103/1.5 mm |
| Cl-[pyridine]-CCl₃, Cl | | M.P. = 125°–127° C. |
| Cl, Cl-[pyridine]-CCl₃ | | M.P. = 37°–41° C. |
| CCl₃-[pyridine]-Cl | | B.P. = 113° C./6 mm |
| Cl-[pyridine]-CCl₃ | | M.P. = 65°–68° C. |
| CCl₃-[pyridine]-Cl | | M.P. = 42°–43° C. |
| Cl-[pyridine]-CCl₃ | | M.P. = 44°–46° C. |

STARTING MATERIALS

The starting materials employed in the process of the present invention are known materials, the preparation of which is taught in the literature or they are articles of commerce.

What is claimed is:

1. A method for converting a carboxylic acid group on the ring of an aryl or nitrogen heteroaromatic compound to a trichloromethyl group which comprises contacting said aryl or nitrogen heteroaromatic compound with a phenylphosphonic dichloride and phosphorus pentachloride in a ratio of from about 0.01:1 to about 10:1 for a time and at a temperature sufficient to carry out the conversion of the carboxylic acid group to a trichloromethyl group.

2. The method as defined in claim 1 wherein the conversion is carried out at a temperature of from about 100° C. to about 250° C.

3. The method as defined in claim 1 wherein the phenylphosphonic dichloride is present in an amount of from about 0.1 to about 20 molar equivalents of the phenylphosphonic dichloride per carboxylic acid group to be converted.

4. The method as defined in claim 3 wherein the amount is from about 1 to about 10 molar equivalents of the phenylphosphonic dichloride per carboxylic acid group.

5. The method as defined in claim 1 wherein the phosphorus pentachloride is present in an amount of from about 2 to about 10 molar equivalents of the phosphorus pentachloride per carboxylic acid group to be converted.

6. The method as defined in claim 1 wherein a carboxylic acid group on an aryl compound is converted.

7. The method as defined in claim 1 wherein a carboxylic acid group on a nitrogen heteroaromatic compound is converted.

8. The method of claim 6 wherein the aryl compound contains one carboxylic acid group.

9. The method of claim 6 wherein the aryl compound contains two carboxylic acid groups in non-sterically hindered ring positions.

10. The method of claim 7 wherein the nitrogen heteroaromatic compound contains one carboxylic acid group.

11. The method of claim 7 wherein the nitrogen heteroaromatic compound contains two carboxylic acid groups in non-sterically hindered ring positions.

12. The method of claim 1 wherein the aryl compound is ring substituted with at least one sterically compatible group from the group consisting of chloro, fluoro, bromo, nitro, cyano, alkyl, alkoxy, alkylthio, hydroxy, aryl, alkyl substituted aryl, alkoxy substituted aryl, aryloxy or trifluoromethyl, with the proviso that when the substituent is alkyl, alkylthio or alkoxy, that a strong electron withdrawing group is also on the ring.

13. The method of claim 1 wherein the nitrogen heteroaromatic compound is ring substituted with at least one sterically compatible group from the group consisting of chloro, fluoro, bromo, nitro, cyano, alkyl, alkoxy, alkylthio, hydroxyl, aryl, alkyl substituted aryl, alkoxy substituted aryl, aryloxy or trifluoromethyl.

* * * * *